(12) United States Patent
Chung et al.

(10) Patent No.: US 9,744,070 B2
(45) Date of Patent: Aug. 29, 2017

(54) SNORING PREVENTION DEVICE

(71) Applicant: Ji-Young Chung, Namyangju-si (KR)

(72) Inventors: Ji-Young Chung, Namyangju-si (KR);
Yeong-Chul Choi, Seoul (KR);
Hye-Young Joung, Namyangju-si (KR)

(73) Assignee: Ji-Young Chung, Gyeonggi-Do (KR)

( * ) Notice: Subject to any disclaimer, the term of this patent is extended or adjusted under 35 U.S.C. 154(b) by 305 days.

(21) Appl. No.: 14/419,232

(22) PCT Filed: Aug. 1, 2013

(86) PCT No.: PCT/KR2013/006953
§ 371 (c)(1),
(2) Date: Feb. 2, 2015

(87) PCT Pub. No.: WO2014/025163
PCT Pub. Date: Feb. 13, 2014

(65) Prior Publication Data
US 2015/0216715 A1 Aug. 6, 2015

(30) Foreign Application Priority Data

Aug. 4, 2012 (KR) .......................... 10-2012-0085465
Nov. 16, 2012 (KR) .......................... 10-2012-0129935

(51) Int. Cl.
*A61F 5/56* (2006.01)
(52) U.S. Cl.
CPC .................................... *A61F 5/566* (2013.01)
(58) Field of Classification Search
CPC ...... A61F 5/56; A61F 5/566; A61F 2005/563; A63B 71/085; A63B 71/086;
(Continued)

(56) References Cited

U.S. PATENT DOCUMENTS 5,409,017 A * 4/1995 Lowe ....................... A61C 7/10
128/848
5,427,117 A * 6/1995 Thornton ................ A61F 5/566
128/848
(Continued)

FOREIGN PATENT DOCUMENTS

CN 2652357 11/2004
DE 20 2010 017 014 2/2011
(Continued)

OTHER PUBLICATIONS

Extended European Search Report dated Mar. 3, 2016 for European Patent Application No. 13828202.5.
(Continued)

*Primary Examiner* — Alireza Nia
*Assistant Examiner* — Caryn Urbanczyk
(74) *Attorney, Agent, or Firm* — Ladas & Parry, LLP

(57) ABSTRACT

A snoring prevention device is provided to be mounted in the mouth to prevent snoring during sleep, to reduce a volume of the device, and to improve a wearing feeling. The snoring prevention device includes an upper jaw mounting frame having an upper tooth insertion groove into which the upper teeth are inserted, and configured to be mounted on the upper jaw, a lower jaw mounting frame having a lower tooth insertion groove into which the lower teeth are inserted, and configured to be mounted on the lower jaw, and a lower jaw advance unit including a push rod provided at the upper jaw mounting frame at a portion of a center of the upper jaw corresponding to the front tooth side such that the lower jaw is advanced by pushing the lower jaw mounting frame forward when the upper jaw and the lower jaw are closed.

2 Claims, 3 Drawing Sheets

(58) Field of Classification Search
CPC ....... A63B 71/088; A63B 23/032; A61C 5/14; A61C 7/08; Y10S 602/902
USPC ........ 128/848, 861, 857, 859, 862; 433/6, 7, 433/11, 19, 24; 602/902
See application file for complete search history.

(56) References Cited

U.S. PATENT DOCUMENTS

| | | | | |
|---|---|---|---|---|
| 5,570,704 | A * | 11/1996 | Buzzard | A61F 5/566 128/848 |
| 6,055,986 | A * | 5/2000 | Meade | A61F 5/566 128/848 |
| 7,766,016 | B2 * | 8/2010 | Orrico | A61F 5/566 128/848 |
| 2003/0217753 | A1 * | 11/2003 | Thornton | A61F 5/566 128/848 |
| 2004/0177853 | A1 * | 9/2004 | Kownacki | A61F 5/566 128/848 |
| 2010/0263677 | A1 * | 10/2010 | Thornton | A61F 5/56 128/848 |
| 2012/0199136 | A1 * | 8/2012 | Urbano | A61F 5/566 128/848 |

FOREIGN PATENT DOCUMENTS

| | | |
|---|---|---|
| JP | 9-502910 A | 3/1997 |
| JP | 2011-5045 | 1/2011 |
| KR | 10-1074536 B1 | 10/2011 |
| WO | 03/011198 | 2/2003 |
| WO | 2006/070805 | 7/2006 |

OTHER PUBLICATIONS

Office Action dated Nov. 17, 2015 for Japanese Patent Application No. 2015-525364 and its English machine translation provided by Applicant's foreign counsel.
International Preliminary Report on Patentability (Chapter I) for PCT/KR2013/006953 issued on Feb. 10, 2015 and its English machine translation by Google Translate.
Written Opinion of the International Search Authority for PCT/KR2013/006953 mailed on Nov. 29, 2013 and its English translation from WIPO.
International Search Report for PCT/KR2013/006953 mailed on Nov. 29, 2013.
Office Action dated Sep. 14, 2015 for Chinese Patent Application No. 201380041094.0.

* cited by examiner

[Fig. 1]
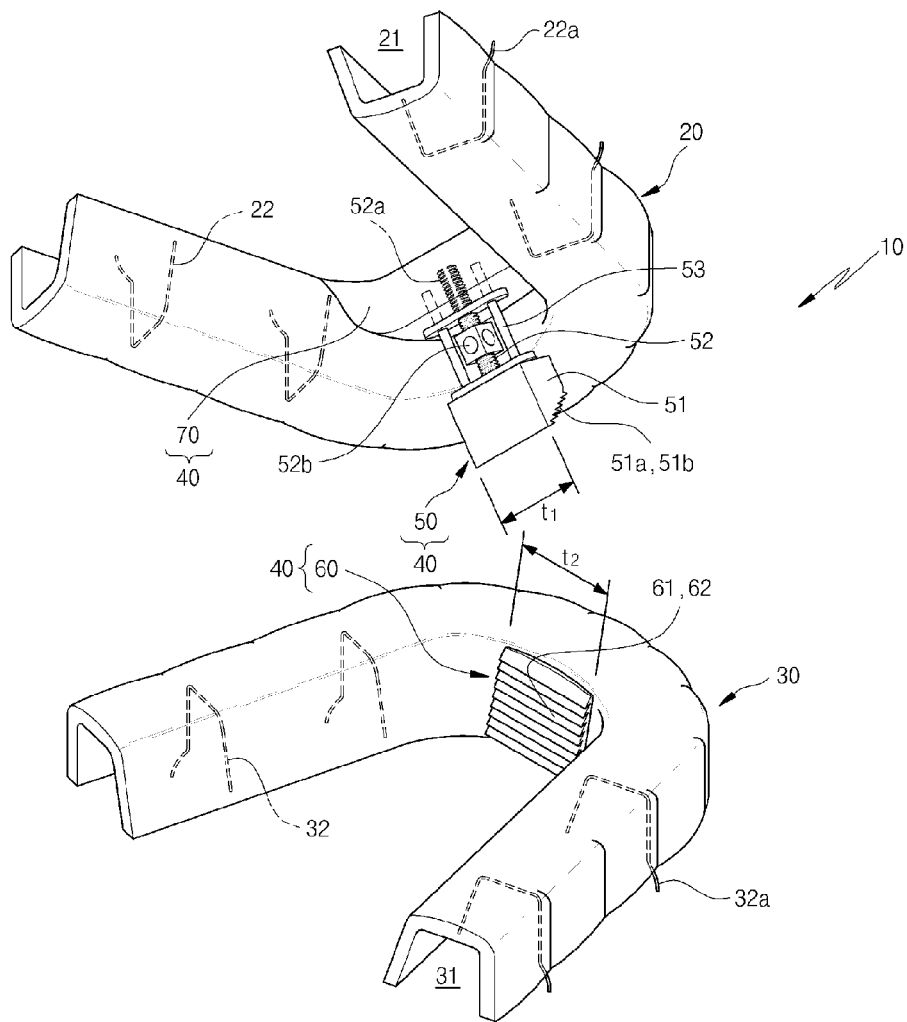
[Fig. 2]
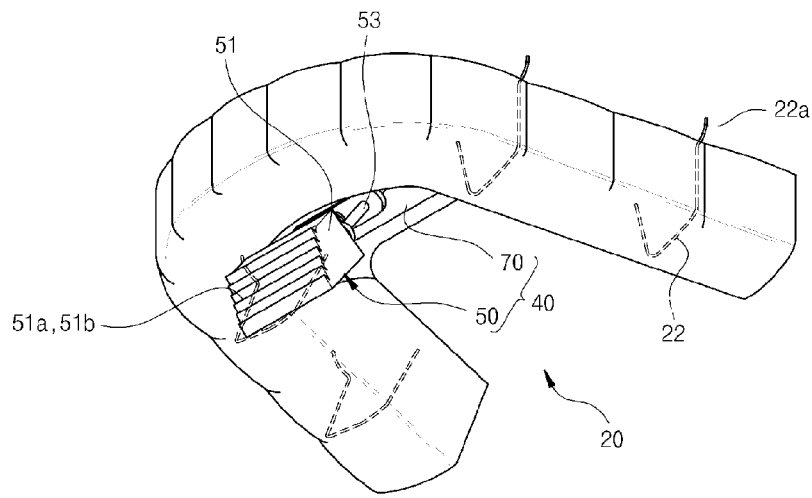

[Fig. 3]
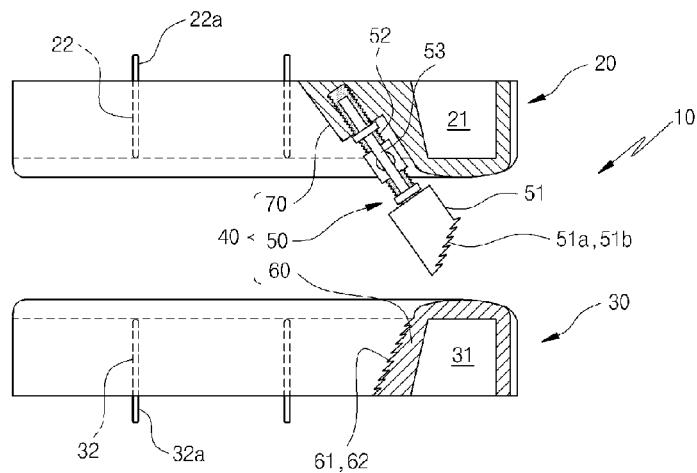
[Fig. 4]
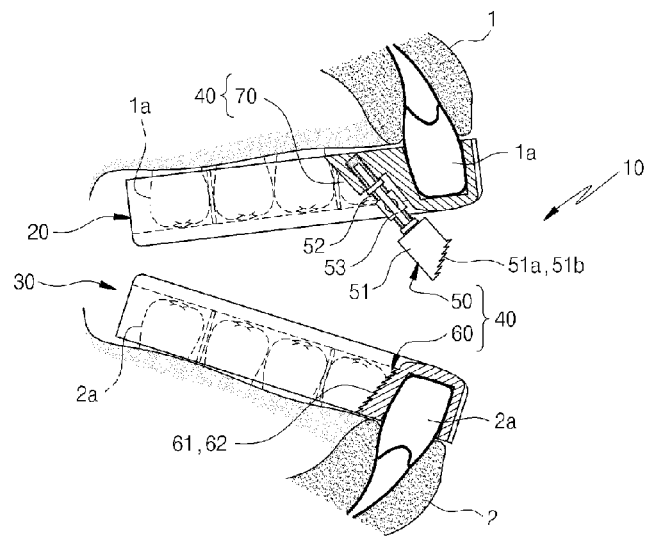
[Fig. 5]
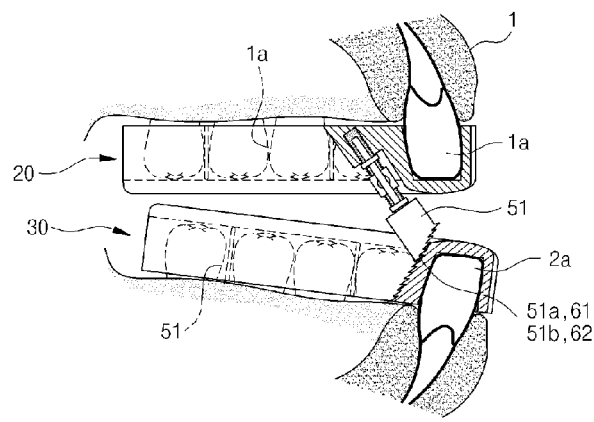

[Fig. 6]
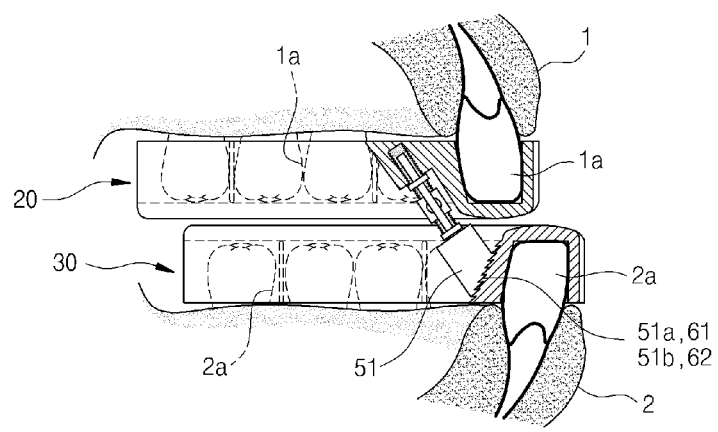

SNORING PREVENTION DEVICE

CROSS-REFERENCE TO RELATED APPLICATION

This application is the U.S. National Stage of International Patent Application No. PCT/KR2013/006953, filed on Aug. 1, 2013, which claims the priority and benefit of Korean Patent Application Nos. 10-2012-0085465, filed on Aug. 4, 2012 and 10-2012-0129935 filed on Nov. 16, 2012, entitled "Snoring Prevention Device" which are hereby incorporated by reference in their entireties into this application.

TECHNICAL FIELD

The present invention relates to a snoring prevention device, and more particularly, to a snoring prevention device provided to be mounted in the mouth to prevent snoring during sleep.

BACKGROUND ART

Snoring is a breathing noise generated by relaxed peripheral structures of the soft palate and the uvula vibrating while a current of breathing air passes through the airway that is narrowed due to various causes during sleep.

In obese persons, the airway is also affected by obesity and becomes narrower, and thus the recent rise in obesity has caused an abrupt increase in the number of patients with snoring difficulties.

Such snoring may often develop into sleep apnea in which apnea frequently occurs during sleep. Severe snoring may cause sleep disturbances such as excessive daytime sleepiness and the like.

In addition, hypoxia during sleep caused due to sleep apnea may cause various complications in the cardiovascular pulmonary vascular system.

Accordingly, as interest in treatments for snoring has increased in recent times, methods of maintaining a patient's airway in an expanded state during sleep and apparatuses related thereto are being developed and proposed in various types. Most conventional snoring prevention devices are provided to be mounted in the mouth during sleep.

Most of the mouth-mounted snoring prevention devices of the related art generally include an upper jaw mounting frame configured to be fitted onto the upper jaw, a lower jaw mounting frame configured to be fitted onto the lower jaw, and a lower jaw advance unit configured to push the lower jaw mounting frame forward to advance the lower jaw and expand the airway in a state in which the upper jaw and the lower jaw are closed. Generally, the pair of lower jaw advance units are formed at both of the upper jaw mounting frame and the lower jaw mounting frame, and the upper jaw mounting frame and the lower jaw mounting frame are fixed by a fixing jig to maintain an advanced state of the lower jaw mounting frame in a state in which the lower jaw mounting frame is advanced by the lower jaw advance unit.

However, since the pair of mouth-mounted snoring prevention devices should be installed at left and right sides of the lower jaw advance unit and the fixing jig should be separately provided, a volume of the device is increased and a feeling of irritation occurs when the device is mounted in the mouth.

In addition, in the conventional snoring prevention device having the pair of lower jaw advance units disposed at both of the upper and lower jaw mounting frame, since lateral movement between the lower jaw mounting frame and the upper jaw mounting frame is limited by the lower jaw advance units of both left and right sides of the lower jaw, it becomes almost impossible to decrease a wearing sensation in the lateral movement of the upper jaw and the lower jaw.

SUMMARY OF INVENTION

Technical Problem

An object of the present invention is to provide a snoring prevention device provided to be mounted in the mouth to prevent snoring during sleep, to reduce a volume of the device, and to improve a wearing sensation.

In addition, another object of the present invention is to provide a snoring prevention device provided to easily move in both left and right directions of the upper jaw and the lower jaw when worn in the mouth.

Solution to Problem

In order to achieve the aforementioned objects, a snoring prevention device includes: an upper jaw mounting frame having an upper tooth insertion groove into which the upper teeth are inserted, and configured to be mounted on the upper jaw; a lower jaw mounting frame having a lower tooth insertion groove into which the lower teeth are inserted, and configured to be mounted on the lower jaw; and a lower jaw advance unit including a push rod provided at the upper jaw mounting frame at a portion of a center of the upper jaw corresponding to the front tooth side such that the lower jaw is advanced by pushing the lower jaw mounting frame forward when the upper jaw and the lower jaw are closed.

The push rod may be installed at the upper jaw mounting frame at an inner side of the front teeth of a center of the upper jaw in an inclined manner such that a front end of the push rod protrudes downward from the front teeth of the center of the upper jaw, and the lower jaw advance unit may further include a section to be pushed provided at the lower jaw mounting frame of a portion of the center of the lower jaw corresponding to the inner side of the front teeth such that the section to be pushed is pushed by the push rod when the upper jaw and the lower jaw are closed.

A first inclined surface may be formed at a front end of the push rod to be inclined downward from an upper portion toward the inside of the mouth, and a second inclined surface may be formed at the section to be pushed to be inclined upward from a lower portion toward the outside of the mouth to come in sliding contact with the first inclined surface during a process of closing the upper jaw and the lower jaw.

A plurality of first serrations may be formed at the first inclined surface along the inclined surface, and a plurality of second serrations may be formed at the second inclined surface along the inclined surface, and the first serrations and the second serrations may be formed to be meshed with each other, and provided to allow relative sliding between the first inclined surface and the second inclined surface in a direction in which the upper jaw and the lower jaw are closed, and restrict relative sliding between the first inclined surface and the second inclined surface in a direction in which the upper jaw and the lower jaw are closed in the meshed state.

The first serration may be formed to protrude upward and toward the outside of the mouth, and the second serration may be formed to protrude downward and toward the inside of the mouth.

The first and second serrations may be formed to have a plurality of rows at the first and second inclined surfaces to adjust an advance level of the lower jaw according to a closing level between the upper jaw and the lower jaw.

The first and second serrations may have different horizontal lengths.

An installation section may be formed at the upper jaw mounting frame at the inner side of the front teeth of the center of the upper jaw such that the push rod is installed, and the push rod may include a body configured to push the section to be pushed, and a pitch adjustment screw having one end rotatably fixed to the body and the other end threadedly coupled to the installation section to advance and retreat such that a protrusion level of the body is adjusted.

Advantageous Effects of Invention

According to an aspect of the present invention, the snoring prevention device includes the lower jaw advance unit disposed at a center between the upper jaw mounting frame and the lower jaw mounting frame to push the lower jaw mounting frame to advance the lower jaw when the upper jaw and the lower jaw are closed.

Accordingly, the snoring prevention device has an overall simplified compact structure according to a decrease in number of the lower jaw advance units such that the wearer can feel less irritation when wearing it in his or her mouth.

In addition, since the snoring prevention device having the lower jaw advance unit disposed at the center between the upper jaw mounting frame and the lower jaw mounting frame can more freely secure lateral movement between the upper jaw and the lower jaw through the lower jaw advance unit without interference with lateral movement of the upper jaw mounting frame and the lower jaw mounting frame, the wearer can wear it more comfortably.

BRIEF DESCRIPTION OF DRAWINGS

FIG. 1 is a perspective view showing a structure of a snoring prevention device according to an embodiment of the present invention;

FIG. 2 is a perspective view showing an upper jaw mounting frame of the snoring prevention device shown in FIG. 1 when seen in a direction different from that of FIG. 1;

FIG. 3 is a cross-sectional view showing the structure of the snoring prevention device according to the embodiment of the present invention;

FIG. 4 is a cross-sectional view showing a state in which the upper jaw mounting frame and the lower jaw mounting frame of the snoring prevention device according to the embodiment of the present invention are mounted on the upper jaw and the lower jaw;

FIG. 5 is a view showing a state in which the upper jaw and the lower jaw are closed and the lower jaw advances from the state of FIG. 4; and FIG. 6 is a view showing a state in which the upper jaw and the lower jaw are completely closed from the state of FIG. 5.

DESCRIPTION OF EMBODIMENTS

Hereinafter, an embodiment of the present invention will be described in detail with reference to the accompanying drawings. The embodiment described below is exemplarily provided such that matters of the present invention can be sufficiently conveyed to those skilled in the art. The present invention is not limited to the following embodiment but may be provided in other forms. For the purpose of clear description of the present invention, illustration of elements not related to the description is omitted, and widths, lengths, thicknesses, and so on, of the elements may be exaggerated for the convenience of illustration. The same reference numerals designate the same elements throughout the specification.

As shown in FIGS. 1 to 3, a snoring prevention device 10 according to the embodiment is provided to be mounted in the mouth to prevent snoring during sleep, and includes an upper jaw mounting frame 20 configured to be mounted on the upper jaw 1 and a lower jaw mounting frame 30 configured to be mounted on the lower jaw 2.

The upper and lower jaw mounting frames 20 and 30 are provided to correspond to a shape of the upper jaw 1 or the lower jaw 2 to form substantially a "U" shape in a planar shape, and may be formed of various harmless materials such as a synthetic resin, silicon, or the like.

An upper tooth insertion groove 21 that is open upward and both leftward and rightward is formed in an upper inner side of the upper jaw mounting frame 20 such that the upper teeth 1a are inserted thereinto, and a lower tooth insertion groove 31 open downward and both leftward and rightward is formed in a lower inner side of the lower jaw mounting frame 30 such that the lower teeth 2a are inserted thereinto.

The upper and lower jaw mounting frames 20 and 30 may be provided such that all the teeth disposed at the upper jaw 1 or the lower jaw 2 are inserted or only some teeth disposed at a center and both sides are inserted.

Since a shape or arrangement of teeth may differ according to a wearer, the upper and lower jaw mounting frames 20 and 30 should be custom-made by making a model according to a shape or arrangement of the teeth of the wearer.

A plurality of reinforcement frames 22 and 32 formed of a metal material are installed in the upper jaw mounting frame 20 and the lower jaw mounting frame 30 around the upper tooth insertion groove 21 and the lower tooth insertion groove 31, and one ends of the reinforcement frames 22 and 32 extend outward from the upper jaw mounting frame 20 and the lower jaw mounting frame 30 to form hooking sections 22a and 32a. The hooking sections 22a and 32a are inserted between the teeth of the wearer when he or she wears the upper and lower jaw mounting frames 20 and 30 such that the upper and lower jaw mounting frames 20 and 30 can be more stably mounted at the upper jaw 1 and the lower jaw 2.

In addition, the snoring prevention device 10 includes a lower jaw advance unit 40 configured to push the lower jaw mounting frame 30 to move the lower jaw 2 forward when the upper jaw 1 and the lower jaw 2 are closed in a state in which the upper and lower jaw mounting frames 20 and 30 are mounted in the mouth of the wearer.

The lower jaw advance unit 40 of the embodiment is solely configured at a center between the upper and lower jaw mounting frames 20 and 30 at a portion corresponding to the front tooth side of the upper jaw 1 and the lower jaw 2 to simplify the overall configuration of the snoring prevention device 10. Accordingly, the snoring prevention device 10 is provided to have a compact size through simplification of the elements such that the wearer feels less irritation when wearing the device in his or her mouth.

In addition, since lateral movement of the upper jaw 1 and the lower jaw 2 is secure because the lower jaw advance unit 40 disposed at the center of the upper and lower jaw mounting frames 20 and does not interfere with the lateral movement between the upper jaw mounting frame 20 and the lower jaw mounting frame 30, the snoring prevention device 10 can limit operations of the upper jaw 1 and the lower jaw 2 relatively less and further improve the overall wearing feeling.

Next, the structure of the lower jaw advance unit 40 will be described in detail.

The lower jaw advance unit 40 includes a push rod 50 installed at the upper jaw mounting frame 20 at the inner side of the front teeth of the center of the upper jaw 1 in an inclined manner to protrude downward from the front teeth of the center of the upper jaw 1, and a section to be pushed 60 provided at the lower jaw mounting frame 30 at a portion corresponding to the inner side of the front teeth of the center of the lower jaw 2 to be pushed forward by the push rod 50 when the upper jaw 1 and the lower jaw 2 are closed. An installation section 70 is formed at the upper jaw mounting frame 20 at the inner side of the front teeth of the center of the upper jaw 1 such that the push rod 50 is installed there. Accordingly, the push rod 50 is installed to be inclined forward and downward from the installation section 70 at the inner side of the front teeth of the upper jaw 1 toward the front teeth.

Generally, when the upper jaw 1 and the lower jaw 2 are opened, the airway may expand and cause mouth breathing, which may easily irritate the wearer. As described above, there is no need to secure a thickness of the upper jaw mounting frame 20 at which the push rod 50 is installed immediately under the front teeth of the upper jaw 1 in a state in which the push rod 50 configured to advance the lower jaw 2 is installed through the installation section 70 at the inner side of the front teeth of the upper jaw 1, and thus the upper jaw mounting frame 20 under the upper tooth insertion groove 21 can be configured to have a relatively small thickness. Accordingly, the snoring prevention device 10 can be designed to maximally reduce a distance between tooth surfaces of the upper jaw 1 and the lower jaw 2, and thus expansion of the mouth can be effectively suppressed in a state in which the upper jaw 1 and the lower jaw 2 are closed, further reducing the irritation that the wearer may feel.

The push rod 50 includes a body 51 configured to push the section to be pushed 60, and a pitch adjustment screw 52 having one end rotatably fixed to the body 51 and the other end provided with a threaded section 52a to be threadedly coupled to the installation section 70 to move forward and rearward such that an advance level of the lower jaw mounting frame 30 is adjusted by the push rod 50 through adjustment of a protrusion level of the body 51.

A tool insertion hole 52b into which a rotary tool is configured to be inserted when the pitch adjustment screw 52 is to be rotated is formed in a center of the pitch adjustment screw 52, and the pitch adjustment screw 52 is coupled to the installation section 70 in a state in which the threaded section 52a is designed to advance or retreat by 1 mm with every four revolutions. The pitch adjustment screw 52 is rotatable in both directions, and the protrusion level of the body 51 is adjusted as the body 51 retreats toward the installation section 70 or advances toward the section to be pushed 60 according to a rotational direction of the pitch adjustment screw 52. A pair of guide bars 53 are installed between the installation section 70 and the body 51 at both sides of the pitch adjustment screw 52 such that the body 51 is not rotated with the pitch adjustment screw 52 upon rotation of the pitch adjustment screw 52. The guide bar 53 has one end fixed to the installation section 70 and the other end slidably fastened to the body 51 to guide movement of the body 51 according to rotation of the pitch adjustment screw 52.

The body 51 of the push rod 50 or the installation section 70 and the section to be pushed 60 may be formed of the same material as the upper and lower jaw mounting frames 20 and 30. The body 51, which is separately manufactured, is connected to the upper jaw mounting frame 20 through the pitch adjustment screw 52) and the guide bar 53, and the installation section 70 and the section to be pushed 60 may be integrally formed with the upper and lower jaw mounting frames 20 and 30 upon manufacture of the upper and lower jaw mounting frames 20 and 30.

In addition, a first inclined surface 51a is provided at a front end of the body 51 of the push rod 50 to be inclined downward from an upper section thereof toward the inside of the mouth such that the section to be pushed 60 is more smoothly pushed by the push rod 50 during a process of closing the upper jaw 1 and the lower jaw 2, and a second inclined surface 61 is provided at the section to be pushed 60 to be inclined upward from a lower section thereof toward the outside of the mouth such that the second inclined surface 61 comes in sliding contact with the first inclined surface 51a during a process of closing the upper jaw 1 and the lower jaw 2.

Accordingly, when the wearer wearing the snoring prevention device 10 closes his or her upper jaw 1 and lower jaw 2, the push rod 50 and the section to be pushed 60 come in sliding contact with each other through the first and second inclined surfaces 51a and 61, and thus the section to be pushed 60 can be smoothly pushed in an advance direction through the body 51.

In addition, a first serration 51b is formed at the first inclined surface 51a, and a second serration 62 is formed at the second inclined surface 61. The first serration 51b and the second serration 62 are formed at the first and second inclined surfaces 51a and 61 in the horizontal direction such that they do not restrict lateral movement between the upper jaw 1 and the lower jaw 2, and the first serration 51b and the second serration 62 are formed at the inclined surfaces 51a and 61 to form a plurality of rows.

The first serration 51b and the second serration 62 may have different lengths such that relative lateral movement between the upper jaw mounting frame 20 and the lower jaw mounting frame 30 can be more smoothly performed. In this embodiment, a length t1 of the first serration 51b is 8 mm and a length t2 of the second serration 62 is 12 mm such that the length of the second serration 62 is relatively large.

The first serration 51b is provided to protrude upward in an inclined direction toward the outside of the mouth and the second serration 62 is provided to protrude downward in an inclined direction toward the inside of the mouth such that a hooking structure is formed in an opening direction of the upper jaw 1 and the lower jaw 2.

Accordingly, the first serration 51b and the second serration 62 allow relative sliding between the first inclined surface 51a and the second inclined surface 61 in a closing direction of the upper jaw 1 and the lower jaw 2 to smoothly guide a closing operation of the upper jaw 1 and the lower jaw 2.

In addition, the first serration 51b and the second serration 62 form a hooking structure in the opening direction of the upper jaw 1 and the lower jaw 2 in a state in which the upper jaw 1 and the lower jaw 2 are hooked to be engaged with each other to restrict relative movement between the first inclined surface 51a and the second inclined surface 61, and thus, even when the wearer is sleeping with his or her mouth closed and his or her lower jaw 2 advanced, and unconsciously opens his or her mouth, the snoring prevention device 10 can stably maintain the advanced state of the lower jaw 2 as the upper jaw 1 and the lower jaw 2 are kept in the closed state by the hooking structure between the first and second serrations 51b and 62. Accordingly, since the snoring prevention device 10 according to the embodiment can safely maintain the advanced state of the lower jaw mounting frame 30 without a separate fixing jig configured to fix the upper jaw mounting frame 20 and the lower jaw mounting frame 30 in the closed state, a more simplified structure can be provided due to omission of the fixing jig.

In addition, as described above, in a state in which the first and second serrations 51b and 62 are configured to form the plurality of rows at the first and second inclined surfaces 51a and 61, in a structure in which the relative sliding between the first and second inclined surfaces 51a and 61 is allowed in the closing direction of the upper jaw 1 and the lower jaw 2 and restricted in the opening direction of the upper jaw 1 and the lower jaw 2, an advance level of the lower jaw 2 can be adjusted according to the closing level between the upper jaw 1 and the lower jaw 2.

Of course, when the wearer intentionally advances his or her lower jaw 2, since the hooking structure between the first and second serrations 51b and 62 can be released, the upper jaw mounting frame 20 and the lower jaw mounting frame 30 can be rapidly removed from the mouth through a simple separating process upon necessity.

Next, an operation of the snoring prevention device will be described with reference to FIGS. 4 to 6.

As shown in FIG. 4a, when the wearer wearing the snoring prevention device 10 closes his or her upper jaw 1 and lower jaw 2, the body 51 of the push rod 50 and the section to be pushed 60 start to come in sliding contact with each other through the first and second inclined surfaces 51a and 61 as shown in FIG. 4b. From this point, the lower jaw mounting frame 30 starts to be gradually pushed forward.

In addition, as shown in FIG. 4c, when the upper jaw 1 and the lower jaw 2 are completely closed, the lower jaw mounting frame 30 is pushed forward in a maximally set state while completing the sliding contact between the first and second inclined surfaces 51a and 61. Here, the upper jaw mounting frame 20 and the lower jaw mounting frame 30 are fixed in the closed state through the hooking action between the first and second serrations 51b and 62 without opening of the upper jaw 1 and the lower jaw 2. Accordingly, the snoring prevention device 10 continuously and safely maintains the advanced state of the lower jaw 2 such that the airway of the wearer is expanded. In this state, when the snoring prevention device 10 is to be removed from the mouth, the wearer intentionally pushes his or her lower jaw 2 to release the hooking structure between the first and second serrations 51b and 62, and in this state, the wearer opens his or her mouth to extract the upper jaw mounting frame 20 and the lower jaw mounting frame 30 from his or her mouth to simply remove the snoring prevention device 10 therefrom.

INDUSTRIAL APPLICABILITY

In recent times, in non-surgical snoring treatment performed in dental clinics, otorhinolaryngology clinics, oriental medical clinics, and the like, mouth-mounted snoring prevention devices have been widely used. However, patent fees must be paid to foreign enterprises having exclusive technologies to use these. Accordingly, the present invention is expected to entirely reduce snoring treatment cost through localization of the mouth-mounted snoring prevention device, and contribute to improvement of the domestic industry through export of the snoring prevention device.

The invention claimed is:

1. A snoring prevention device comprising:
   an upper jaw mounting frame having an upper tooth insertion groove, configured for upper teeth to be inserted therein and configured to be mounted on an upper jaw;
   a lower jaw mounting frame having a lower tooth insertion groove, configured for lower teeth to be inserted therein and configured to be mounted on a lower jaw; and
   a lower jaw advance unit including a push rod provided at a center of an upper and inner side of the upper jaw mounting frame such that the lower jaw is advanced by pushing the lower jaw mounting frame forward when the upper jaw and the lower jaw are closed and a section to be pushed provided at a center of the lower jaw mounting frame such that the section to be pushed is pushed forward by the push rod when the upper jaw and the lower jaw are closed,
   wherein the push rod is installed at the center of the upper and inner side of the upper jaw mounting frame in an inclined manner such that a front end of the push rod protrudes downward from the center of the upper jaw mounting frame, an installation section is formed at the center of the inner side of the upper jaw mounting frame, such that the push rod is installed, and the section to be pushed is disposed at a center of an inner side of the lower jaw mounting frame,
   a first inclined surface is formed at the front end of the push rod to be inclined downward from an upper portion toward the inside of a mouth, and a second inclined surface is formed at the section to be pushed to be inclined upward from a lower portion toward the outside of the mouth to come in sliding contact with the first inclined surface during a process of closing the upper jaw and the lower jaw,
   first serrations and second serrations are formed to be meshed with each other, and provided at the first inclined surface and the second inclined surface to allow relative sliding between the first inclined surface and the second inclined surface in a direction in which the upper jaw and the lower jaw are closed, and restrict relative sliding between the first inclined surface and the second inclined surface in a direction in which the upper jaw and the lower jaw are opened,
   the first serration is formed on the first inclined surface of the push rod to inclinedly protrude upward and toward the outside of the mouth, and the second serration is formed on the second inclined surface of the lower jaw mounting frame to inclinedly protrude downward and toward the inside of the mouth to restrict an opening operation between the first inclined surface and the second inclined surface before a wearer intentionally further pushes the lower jaw forward in a state in which the first serrations and the second serrations are meshed with each other, and
   the first and second serrations are formed to form a plurality of rows at the first and second inclined surfaces to adjust an advance level of the lower jaw according to a closing level between the upper jaw and the lower jaw.

2. The snoring prevention device according to claim 1, wherein the push rod comprises a body configured to push the section to be pushed, and a pitch adjustment screw having one end rotatably fixed to the body and an other end threadedly coupled to the installation section to advance and retreat such that a protrusion level of the body is adjusted.

* * * * *